(12) United States Patent
Maxy et al.

(10) Patent No.: US 7,520,887 B2
(45) Date of Patent: Apr. 21, 2009

(54) INTERSPINOUS DEVICE FOR IMPEDING THE MOVEMENTS OF TWO SUCCESSIVE VERTEBRAE, AND METHOD FOR MAKING A PAD DESIGNED FOR IT

(75) Inventors: Philippe Maxy, Claye Couilly (FR); Jose Gournay, Dammartin en Goele (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 221 days.

(21) Appl. No.: 10/546,335

(22) PCT Filed: Feb. 17, 2004

(86) PCT No.: PCT/IB2004/000390

§ 371 (c)(1),
(2), (4) Date: Jan. 3, 2006

(87) PCT Pub. No.: WO2004/073533

PCT Pub. Date: Sep. 2, 2004

(65) Prior Publication Data

US 2006/0217726 A1 Sep. 28, 2006

(30) Foreign Application Priority Data

Feb. 19, 2003 (FR) .................................. 03 02038

(51) Int. Cl.
*A61B 17/70* (2006.01)
*A61B 17/82* (2006.01)
*A61F 2/44* (2006.01)

(52) U.S. Cl. .................... 606/248; 606/74; 606/910; 606/263; 623/17.11

(58) Field of Classification Search .................. 606/61, 606/248, 249; 623/13.11, 13.13, 13.14, 17.11–17.16
See application file for complete search history.

(56) References Cited

U.S. PATENT DOCUMENTS 1,599,564 A * 9/1926 Fowler ........................ 428/103
5,496,318 A * 3/1996 Howland et al. .............. 606/61

(Continued)

FOREIGN PATENT DOCUMENTS

| FR | 2 775 183 | 8/1999 |
| FR | 2 818 530 | 6/2002 |
| FR | 2 844 179 | 3/2004 |
| WO | WO 99/42051 | * 8/1999 |
| WO | WO 03/015645 | 2/2003 |

OTHER PUBLICATIONS

Patent Cooperation Treaty, "PCT International Search Report," International Application No. PCT/IB2004/000390, Jun. 4, 2004, 7 pages.

* cited by examiner

*Primary Examiner*—Eduardo C Robert
*Assistant Examiner*—Jay R Sigler
(74) *Attorney, Agent, or Firm*—Coats and Bennett, P.L.L.C.

(57) ABSTRACT

An interspinous device for impeding the movements of two successive vertebrae (8, 9) of the spinal column. In some embodiments, the device includes two pads (2a, 2b; 11a, 11b; 20a, 20b) whose internal faces (3a, 3b; 12a, 12b) are intended to be pressed against the lateral faces of the spinous processes (6, 7) of the vertebrae (8, 9), and ligaments (4, 5a, 5b, 5c, 5d; 17a, 17b, 18, 19; 23, 24) which connect the pads (2a, 2b; 11a, 11b; 20a, 20b) to each other and to the spinous processes (6, 7), so that, during flexion and extension movements of the spinal column with respect to its normal position, the pressures exerted against the lateral faces of the spinous processes (6, 7) by the pads (2a, 2b; 11a, 11b; 20a, 20b) increase as the spinal column moves away from the normal position. Method for making a pad designed for such a device.

4 Claims, 2 Drawing Sheets

U.S. PATENT DOCUMENTS

| | | | |
|---|---|---|---|
| 5,609,634 A * | 3/1997 | Voydeville | 623/13.11 |
| 5,836,948 A * | 11/1998 | Zucherman et al. | 606/61 |
| 6,099,527 A * | 8/2000 | Hochschuler et al. | 606/61 |
| 6,187,043 B1 * | 2/2001 | Ledergerber | 623/8 |
| 6,626,944 B1 * | 9/2003 | Taylor | 623/17.16 |
| 6,761,720 B1 * | 7/2004 | Senegas | 606/61 |
| 6,946,000 B2 * | 9/2005 | Senegas et al. | 623/17.11 |
| 7,048,736 B2 * | 5/2006 | Robinson et al. | 606/61 |
| 7,238,204 B2 * | 7/2007 | Le Couedic et al. | 623/17.11 |
| 2001/0016743 A1 | 8/2001 | Zucherman et al. | |
| 2005/0010298 A1 * | 1/2005 | Zucherman et al. | 623/17.16 |
| 2005/0261768 A1 * | 11/2005 | Trieu | 623/17.11 |
| 2006/0085070 A1 * | 4/2006 | Kim | 623/17.11 |
| 2006/0089654 A1 * | 4/2006 | Lins et al. | 606/90 |
| 2006/0089718 A1 * | 4/2006 | Zucherman et al. | 623/17.11 |

INTERSPINOUS DEVICE FOR IMPEDING THE MOVEMENTS OF TWO SUCCESSIVE VERTEBRAE, AND METHOD FOR MAKING A PAD DESIGNED FOR IT

CROSS REFERENCE

This application is a United States national phase application of co-pending international patent application number PCT/IB2004/000390, filed Feb. 17, 2004, which claims priority to French patent application number 03/02038, filed Feb. 19,2003 which priority is claimed.

BACKGROUND

The invention relates to the field of surgical implants intended to impede the coming-together of two vertebrae during movements of the spinal column.

When intervertebral discs have been subject to considerable wear or degeneration, they may become powerless to prevent excessive coming-together of two successive vertebrae during flexion (forward movement) or extension (backward movement) of the spinal column. Such coming-together may have the consequence of crushing the spinal nerves, which is very painful for the patient. In the most serious cases, this coming-together may continue until the vertebrae contact one another during extreme movements.

A first known method for solving this problem consists in fastening one of the vertebrae in question to the other, so as to keep a space between them which is permanently enough. This fastening may be carried out by means of various devices in the form of plates. However, it causes a significant loss of mobility for the patient, because it prohibits any flexion or extension of the spinal column in the region in question.

It is also known to ligature the spinous processes of the vertebrae in question by means of artificial ligaments. This makes it possible to retain freedom of movement in extension for the vertebrae while limiting the magnitude of the allowed flexions, to the extent of prohibiting contact between the front of the vertebrae. However, this does not prevent contact at the back of the vertebrae, although this region is where compression of the spinal nerves is most likely to occur.

It is also known to insert interspinous wedges between the spinous processes, as in document EP-A-0 392 124. These wedges are made of a rigid material such as PTFE, and thus prevent any contact between the spinous processes that they separate during extension of the spinal column. Preferably, they are held in place by artificial ligaments which pass through them and are wound around the spinous processes. By virtue of these ligaments, it is also possible to limit the magnitude of flexion movements of the spinal column in the region in question.

However, the fact of having a rigid element between the spinous processes leads to virtual removal of the extension movements of the spinal column at that point, or at least to a sudden interruption of such movements when the processes come into contact with the wedge.

It would be desirable to be able to use a device reproducing the normal behaviour of a vertebra-disc-vertebra stack (functional unit) more faithfully, where normally the action of blocking the movements of the spinal column only takes place gradually.

The aim of the invention is to provide a device meeting this requirement.

SUMMARY

To this end, the subject of the invention is an interspinous device for impeding the movements of two successive vertebrae of the spinal column, characterized in that it comprises:
  two pads whose internal faces are intended to be pressed against the lateral faces of the spinous processes of the said vertebrae,
  and ligaments which connect the said pads to each other and to the said spinous processes, so that, during flexion and extension movements of the spinal column from its normal position, the pressures exerted against the lateral faces of the spinous processes by the said pads increase as the spinal column moves away from the said normal position.

Each of the said pads may have a protuberance intended to penetrate into the interspinous space.

Each of the said pads may consist of a tape folded over and sewn onto itself.

Each of the said pads may consist of a solid object.

The device may comprise a pin passing through transverse perforations in the said pads intended to be placed facing the interspinous space separating the two vertebrae, the said pin having flanges able to bear against the surfaces of the said pads, surfaces turned outwards from the spinal column.

The said ligaments may comprise:
  one ligament in the form of a tape fitting tightly around the pads and having free parts which, when tensioned, make a space having a width "d" greater than a distance separating the interspinous processes of the vertebrae,
  and four ligaments which are each attached to an upper part or to a lower part of a pad.

Each of the said pads may comprise:
  one longitudinal perforation connecting the upper part and the lower part of the pad,
  and two upper and lower transverse perforations connecting the internal face and the external face of the pad, and the device may comprise two ligaments which are each inserted in one of the said longitudinal perforations, one ligament which is inserted in the upper transverse perforations of the said pads and one ligament which is inserted in the lower transverse perforations of the said pads.

In each pad, the said transverse perforations can then intersect the said longitudinal perforation, the ligaments inserted in the longitudinal perforations are in the form of a tape and the said ligaments inserted in the transverse perforations pass through the ligaments inserted in the longitudinal perforations.

Each pad may have a longitudinal perforation connecting the upper part and the lower part of the pad and a ligament inserted in the said longitudinal perforation, one end of which is free and the other end of which is shaped in a loop so that it can be ligatured with the free end of the ligament inserted in the longitudinal perforation of the other pad.

The subject of the invention is also a method for making a pad for such an interspinous device, characterized in that said pad is made by folding back and sewing on itself a tape made of a material such as polyester or an elastomer.

As will be understood, the invention consists in providing an interspinous device whose main elements consist of two elements pressed against the lateral faces of the spinous processes. They are made from a relatively flexible material having properties of compressibility and low elasticity. Polyesters and elastomers, or even some composites, may be used for this purpose. They may have a shape such that they slightly penetrate into the interspinous space at rest. They are held against the processes by artificial ligaments and are connected to each other in order to form an assembly:

- either by the same ligaments which hold them in place against the spinous processes;
- or by an envelope which confines them both at some distance from each other and on which the processes rest when the device is in place;
- or by a centring pin passing through both pads and passing through the interspinous space;
- or by several of these devices at the same time.

The elements are pressed against the spinous processes such that they transmit lateral pressures to them equally well during flexion movements as during extension movements of the spinal column, and also during rotational movements. These pressures increase as the spinal column moves away from its normal position, and end up being sufficiently high to stop the possibility of movement before excessive coming-together of the vertebrae takes place.

BRIEF DESCRIPTION OF THE DRAWINGS

The invention will be better described with the help of the following appended figures.

DETAILED DESCRIPTION

Figure 1A:
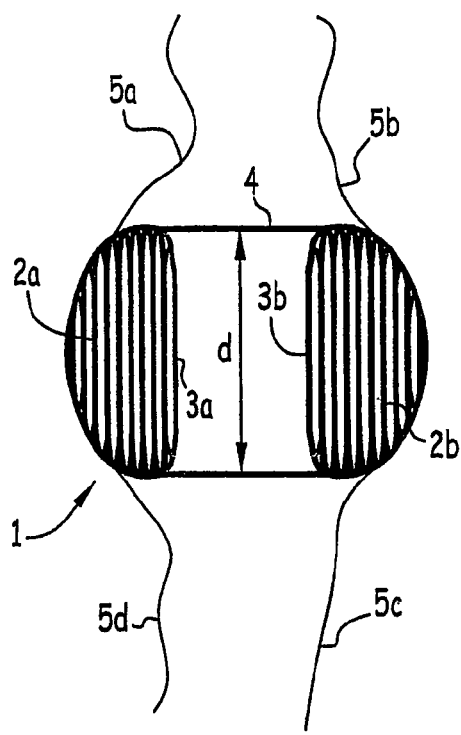
FIGS. 1a, 1b which show a first embodiment of the invention, in the rest state (FIG. 1a) and when placed between two vertebrae (FIG. 1b)
Figure 1B:
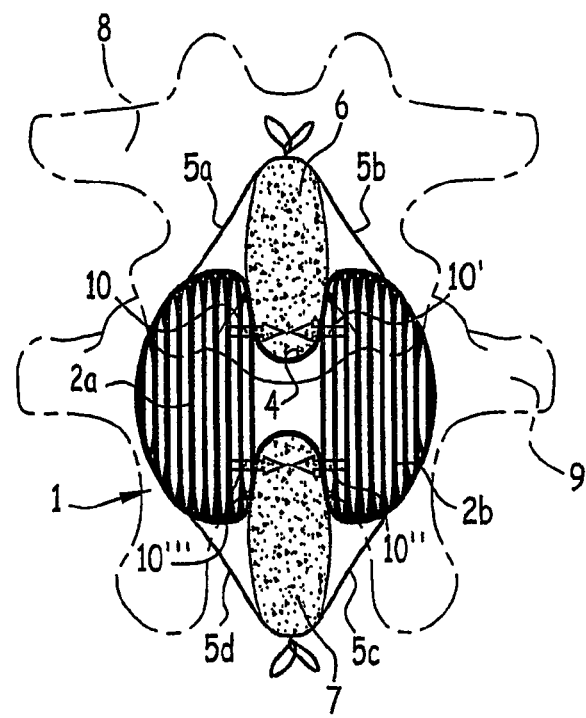
Figure 2A:
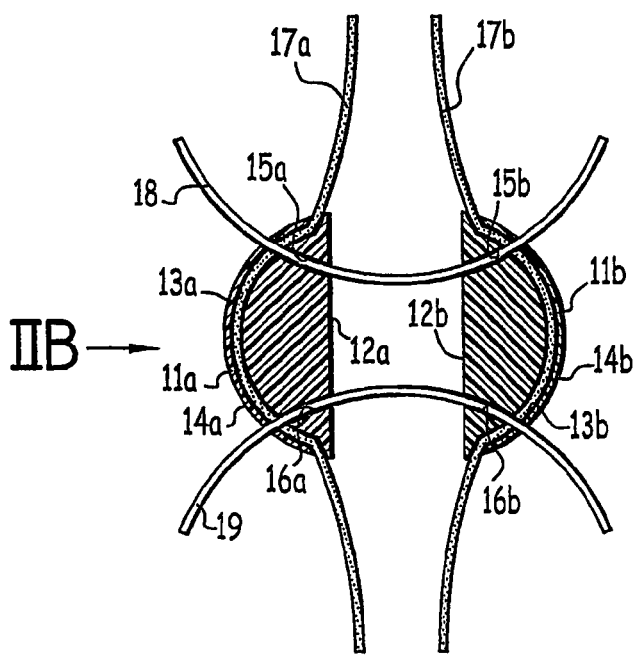
FIGS. 2a, 2b which show a second embodiment of the invention in the rest state, seen from the front in longitudinal section (FIG. 2a) and in profile (FIG. 2b)
Figure 2B:
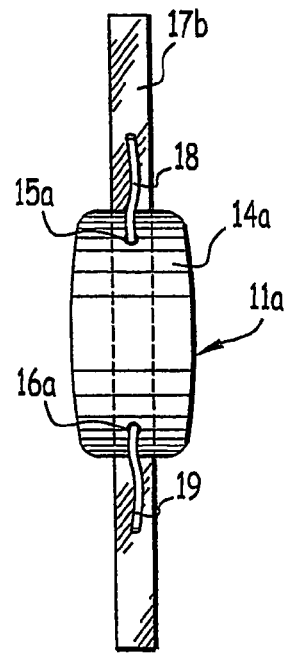

A first embodiment of the invention is shown in FIGS. 1a and 1b. In the rest state (FIG. 1a), the interspinous device 1 is in the form of two pads 2a, 2b, each one having an internal face in the form of a substantially flat surface 3a, 3b intended to rest against the vertebrae when the wedge is put in place. In the example shown, each of these pads 2a, 2b is formed by a tape made of a material having some compressibility and low elasticity, such as polyester or an elastomer, folded over and sewn onto itself in order to form a stack of a general external shape that is, for example, hemispherical, semi-ovoid, or similar. The pads 2a, 2b fit tightly within the same tape-type ligament 4 made of a material comparable to that of the pads 2a, 2b, and the free parts of which connect, on the one hand, the upper parts and, on the other hand, the lower parts of the pads 3a, 3b, and which leaves the flat surfaces 3a, 3b free. This tape 4 itself bears four ligaments 5a, 5b, 5c, 5d which are attached to it in the respective vicinities of the upper and lower parts of the pads 2a, 2b. The tape 4 is fastened to the pads 2a, 2b and, in the rest state, when tensioned, its free parts allow a space of width "d" to be made between the internal surfaces 3a, 3b of the pads 2a, 2b.

When the interspinous device 1 is put in place on the spinous processes 6, 7 of two successive upper 8 and lower 9 vertebrae, it is as shown in FIG. 1b. The device 1 is inserted between the spinous processes 6, 7 which are separated heightwise by a length substantially less than "d". In this way, the lower part of the spinous apophysis 6 of the upper vertebra 8 and the upper part of the spinous apophysis 7 of the lower vertebra 9 tension the tape 4. This tension compresses and brings together the pads 2a, 2b, the flat internal surfaces 3a, 3b of which come into contact with the sides of the spinous processes 6, 7 and exert pressure forces on them in the direction of the arrows 10, 10', 10", 10"'. The placement of the device 1 is completed by ligaturing ligaments 5a, 5b at the upper part of the spinous apophysis 6 of the upper vertebra 8 and ligaments 5c, 5d at the lower part of the spinous apophysis 7 of the lower vertebra 9.

In this way, when the spinal column operates in extension, that is to say when the patient bends backwards, and when the spinous processes 6, 7 tend to come close to each other, the tension exerted on the tape 4 at its free parts tends to increase. The effect of this is to gradually increase the compression of the pads 2a, 2b (especially at their ends) and the pressures exerted by them on the spinous processes 6, 7 in the direction of the arrows 10, 10', 10", 10"'. The dimensional and mechanical characteristics of the various elements of the device 1 are calculated so that the pressures exerted by the pads 2a, 2b on the spinous processes 6, 7 end up becoming enough to stop the coming-together thereof before causing trauma to the spinal nerves passing between the processes 6, 7, as would occur with a healthy functional unit.

On the other hand, when the spinal column operates in flexion, that is to say when the patient bends forwards, and when the spinous processes 6, 7 tend to move away from each other, this has the effect of increasing the tension exerted on the ligaments 5a, 5b, 5c, 5d. This increased tension is transmitted to the tape 4, at its parts which are fastened to the pads 2a, 2b. This has the effect, as in the previous case, of gradually increasing the compression of the pads 2a, 2b and the pressures exerted by them on the spinous processes 6, 7 in the direction of the arrows 10, 10', 10", 10"'. It is necessary that, beyond a certain separation of the spinous processes 6, 7, these pressures become great enough to prevent any further separation which would risk causing trauma, as would occur with a healthy functional unit. The ligaments 5a, 5b, 5c, 5d also play a role in impeding and interrupting the flexion movements of the spinal column, because of their possibilities of limited extension.

As a variant, each of the pads 2a, 2b may be made in the form of a solid object, for example made of silicon lined with polyester, whose faces turned towards the spinous processes 6, 7 may be flat (as in the previous example) or may each have a protuberance slightly penetrating into the inter-apophysis space so that the coming-together movements of the spinous processes 6, 7 can be blocked more efficiently and reliably.

The variant of the invention shown in FIGS. 2a, 2b, 3a, 3b has such pads 11a, 11b, made in the form of solid objects of approximately hemispherical or semi-ovoid shape. In the example shown, each of the pads 11a, 11b have their face 12a, 12b intended to be turned towards the spinous processes 6, 7 which is of flat shape, it being understood that the said faces 12a, 12b could each have a protuberance as described above.

Each of the pads 11a, 11b has a series of perforations intended to allow the passage of the various ligaments making it possible to attach the pads 11a, 11b to the spinous processes 6, 7:

- one longitudinal perforation 13a, 13b which, in the example shown, lies substantially parallel to the periphery of the face 14a, 14b of the pad 11a, 11b intended to be turned away from the spinous processes 6, 7, and connects the upper region to the lower region of the pad 11a, 11b;
- and two transverse perforations 15a, 15b; 16a, 16b, one 15a, 15b located in the upper part of the pad 11a, 11b and the other 16a, 16b located in the lower part of the pad 11a, 11b, which connect the internal faces 12a, 12b and external faces 14a, 14b of the pad 11a, 11b.

In the example shown, the transverse perforations 15a, 15b; 16a, 16b pass through the longitudinal perforations 13a, 13b; however, this configuration is not essential.

Ligaments pass through the various perforations as follows:
   each of the tape-type ligaments 17a, 17b passes through the longitudinal perforation 13a, 13b of one of the pads 11a, 11b;
   one and the same wire-type upper ligament 18 passes through the upper transverse perforation 15a, 15b of each of the pads 11a, 11b;
   and one and the same wire-type lower ligament 19 passes through the lower transverse perforation 16a, 16b of each of the pads 11a, 11b.

In the example shown, each wire ligament 18, 19 passes through the tape-type links 17a, 17b, but it must be understood that this arrangement is not essential, in particular if the transverse perforations (15a, 15b; 16a, 16b) do not pass through the longitudinal perforations 13a, 13b.

Figure 3A:
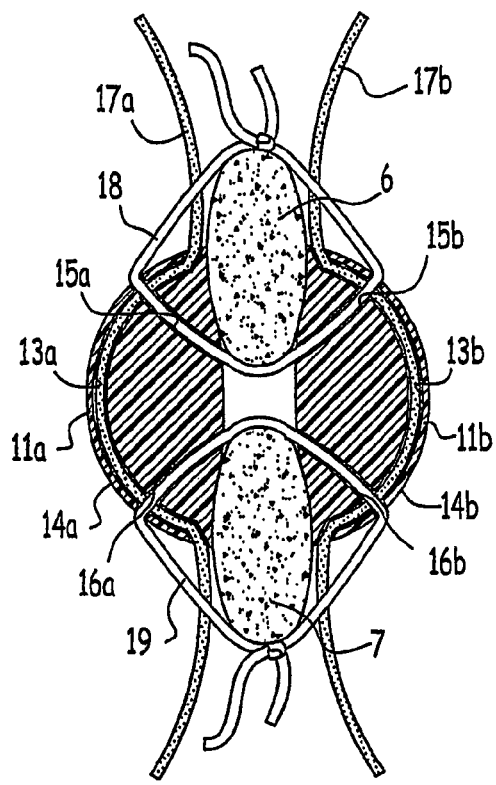
FIGS. 3a and 3b which show, seen in longitudinal section, the second embodiment of the invention at two stages of its placement.
Figure 3B:
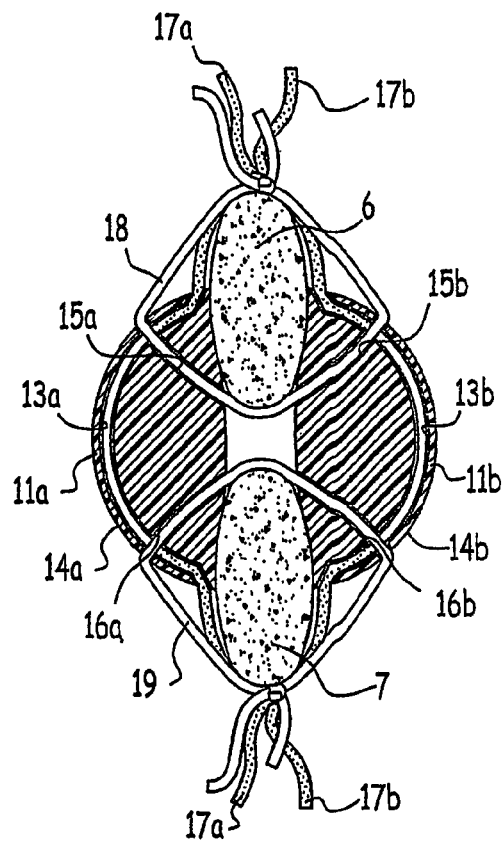

The interspinous device provided by the pads 11a, 11b is implanted, as shown in FIGS. 3a, 3b.

First of all, the pads 11a, 11b are placed against the spinous processes 6, 7 of two successive vertebrae, with the upper wire ligament 18 passing under the apophysis 6 of the upper vertebra, and the lower wire ligament 19 passing over the apophysis 7 of the lower vertebra. The wire ligaments 18, 19 are then ligatured around their respective processes 6, 7, as shown in FIG. 3a.

Secondly, the tape-type ligaments 17a, 17b are tied or fastened to each other at their two ends, as shown in FIG. 3b. This operation finishes putting the pads 11a, 11b in compression against the processes 6, 7, and makes it possible for them to function in a manner comparable to that of the device 1 shown in FIGS. 1a, 1b during flexions and extensions of the spinal column.

Compared to the variant previously described and shown in FIGS. 1a, 1b, this variant has the advantage of not needing the interspinous ligaments to be sectioned for its implantation. The stability of the region concerned of the spinal column is thus improved.

Instead of consisting of solid objects as shown, the pads 11a, 11b could consist of tapes folded back on themselves, like the pads 2a, 2b. Under these conditions, the tape-type ligaments 17a, 17b may simply be fastened to the external faces 14a, 14b of the pads 11a, 11b without being housed in longitudinal perforations 13a, 13b in pads 11a, 11b. Moreover, this configuration could also be adopted with solid pads 11a, 11b.

Figure 4:
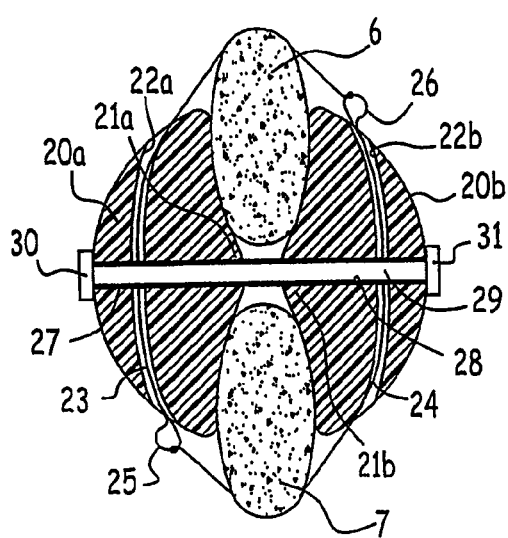
FIG. 4 which shows, seen in longitudinal section, a third embodiment of the invention after its placement.

Another variant of the invention is shown in FIG. 4. In this variant, the interspinous device consists of two pads 20a, 20b, each one of which has a protuberance 21a, 21b able to penetrate into the inter-apophysis space (as has been mentioned, such protuberances may be present on the pads of the other variants which have been described). These pads 20a, 20b have longitudinal perforations 22a, 22b comparable to the longitudinal perforations 13a, 13b of the previous variant. Each of the latter encloses a wire- or tape-type ligament 23, 24, one end 25, 26 of which is shaped into a loop. The ligaments 23, 24 are inserted into the pads 20a, 20b so that one 25 of the loops is placed on the lower face of its pad 20a, and the other 26 on the upper face of its pad 20b. When the interspinous device is put in place, the free end of each ligament 23, 24 is ligatured in the loop 25, 26 of the other ligament 24, 23.

In this way, when the spinal column operates in flexion, the forces exerted by the processes 6, 7 on the ligaments 23, 24 tension the latter and they tend to press the pads 20a, 20b against the processes 6, 7, the movements of which are impeded as in the previous variants. When the spinal column operates in extension, the pads 20a, 20b tend to separate from each other under the effect of the forces exerted by the processes 6, 7 on the protuberances 21a, 21b; however, this separation is impeded by the forces exerted on the ligaments 23, 24. The latter transmit these forces to the extreme parts of the pads 20a, 20b, which tend to be pressed against the processes 6, 7 and therefore impede their coming together. Effects similar to those which have been described for the previous variants thus occur again.

In the example shown in FIG. 4, the interspinous device has another feature which is only optional and which may, likewise, be transposed to the other variants of the invention. Each pad 20a, 20b has a transverse perforation 27, 28 placed substantially in the central region of the pad 20a, 20b. The perforations are intended to face the interspinous space after the device has been put in place and to face each other. A pin 29 made of a rigid or slightly deformable material, fitted at its ends with flanges 30, 31, each one bearing against the surface of a pad 20a, 20b turned outwards from the spinal column, passes through these transverse perforations 27, 28. This pin 29 is inserted into the pads 20a, 20b before or after the interspinous device has been put in place. The prime function of this pin 29 is to provide proper centring of the pads 20a, 20b with respect to one another. It also makes it possible to prevent a lateral expansion of the pads 20a, 20b during the extension movements of the spinal column. The stresses to which the pads 20a, 20b are subject are then transferred to their ends, and this increases the pressure forces exerted on the processes 6, 7.

As a variant, the pin 29 may consist of a protuberance from one of the pads 20a, 20b, penetrating into a transverse perforation of the other pad where it is held by a flange secured to the pin after its insertion into the other pad.

It must be understood that the examples which have been described and shown are not limiting, and that, in particular, it would be possible to transpose to some other variants elements which have only been described for a single one of them if there is no obvious incompatibility which would prevent it.

The invention claimed is:

1. An interspinous device for impeding the movements of two successive vertebrae of the spinal column, comprising:
   a first and second pad, each pad having external and internal faces, said internal faces configured to be pressed against the lateral faces of the spinous processes of the vertebrae,
   a first, second, third, and fourth ligament which together connect the first and second pads to each other and are configured to attach the first and second pads to the spinous processes so that, during flexion and extension movements of the spinal column from its normal position, the pressures exerted against the lateral faces of the spinous processes by the first and second pads increase as the spinal column moves away from the normal position,
   wherein the first and second pads each further comprise:
      one longitudinal perforation connecting the upper part and the lower part of the pad;
      an upper transverse perforation and a lower transverse perforation, each transverse perforation connecting the internal face and the external face of the pad;

wherein said first ligament is inserted in said longitudinal perforation of said first pad;

wherein said third ligament is inserted in the upper transverse perforation of said first and second pads;

wherein said third ligament is inserted in the upper transverse perforation of said first and second;

wherein said fourth ligament is inserted in the lower transverse perforation of said first and second pads;

wherein, in each pad, the upper and lower transverse perforations intersect the longitudinal perforation; and the third and fourth ligaments pass through the first and second ligaments.

2. Device according to claim 1, wherein each of the pads has a protuberance configured to penetrate into the interspinous space.

3. Device according to claim 1, wherein each of the pads comprises of a tape folded over and sewn onto itself.

4. The device according to one of claims 1 and 3 wherein each ligament inserted in the longitudinal perforation includes one end of which is free and the other end of which is shaped in a loop so that it can be ligatured with the free end of the ligament inserted in the longitudinal perforation of the other pad.

* * * * *